United States Patent [19]

Mabille

[11] 4,281,373

[45] Jul. 28, 1981

[54] HIGH FREQUENCY VOLTAGE GENERATOR

[75] Inventor: Pierre Mabille, Bordeaux, France

[73] Assignee: Societe SATELEC, Talence, France

[21] Appl. No.: 906,556

[22] Filed: May 16, 1978

[30] Foreign Application Priority Data

May 18, 1977 [FR] France .................. 77 15246

[51] Int. Cl.³ .................. A61B 17/36; H02M 3/335; H02M 7/537
[52] U.S. Cl. .................. 363/21; 128/303.14; 128/303.17; 363/80; 363/133
[58] Field of Search .................. 128/303.13, 303.14, 128/303.17; 307/358, 359; 323/17, 20, DIG. 1; 363/20, 21, 24, 25, 34, 37, 79, 80, 97, 133

[56] References Cited

U.S. PATENT DOCUMENTS

| 3,365,650 | 1/1968 | Camp et al. | 363/97 |
| 3,636,298 | 1/1972 | Risberg et al. | 323/20 X |
| 3,658,067 | 4/1972 | Bross | 128/303.14 |
| 3,702,434 | 11/1972 | Ryan | 363/37 |
| 3,885,569 | 5/1975 | Judson | 128/303.14 |
| 3,909,702 | 9/1975 | Hart | 323/20 X |
| 4,034,280 | 7/1977 | Cronin et al. | 363/25 |
| 4,126,137 | 11/1978 | Archibald | 128/303.14 |

Primary Examiner—A. D. Pellinen
Attorney, Agent, or Firm—McAulay, Fields, Fisher, Goldstein & Nissen

[57] ABSTRACT

This high frequency voltage generator which may be used particularly in surgery for supplying an electric bistoury, comprises a power oscillator operating an output transformer. A chopping supply is placed in the direct control chain of the power oscillator. The output voltage of the generator is controlled by a first regulation loop whose reference value is increased by means of a positive feedback proportional to the output current.

7 Claims, 7 Drawing Figures

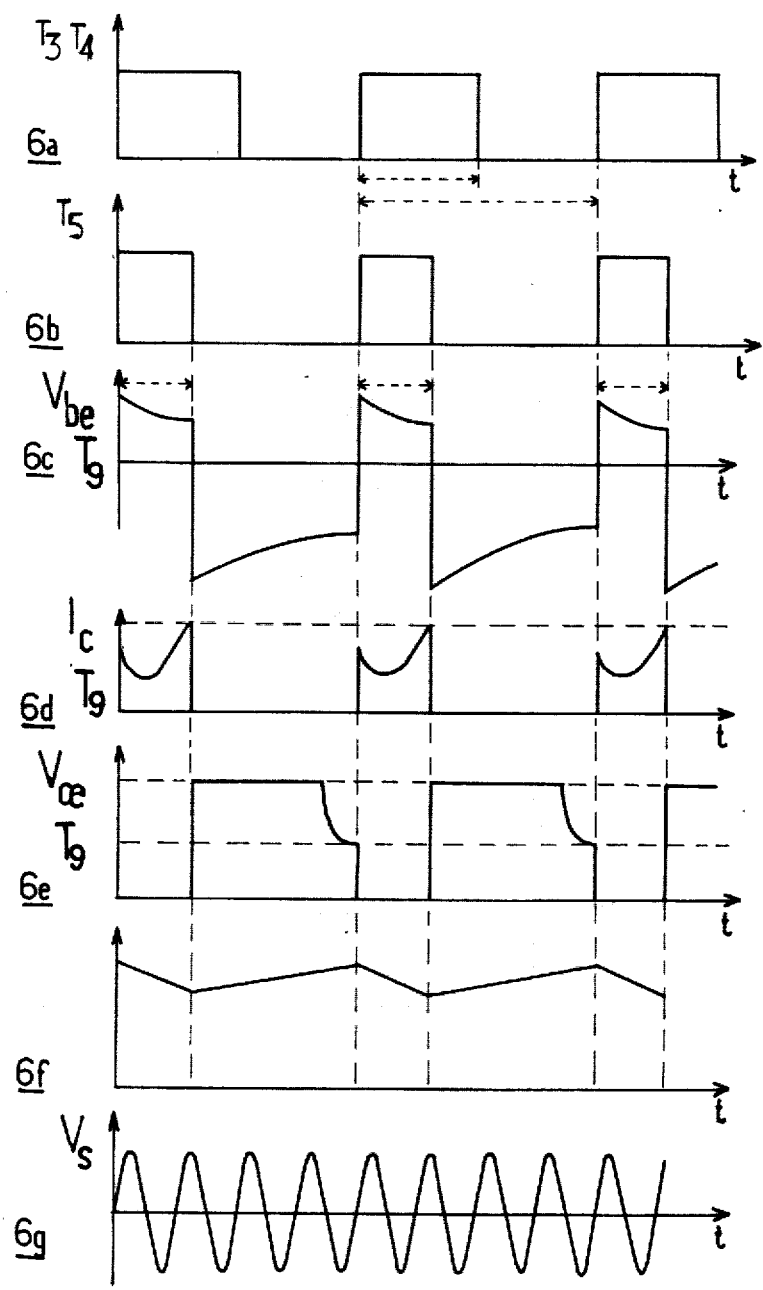

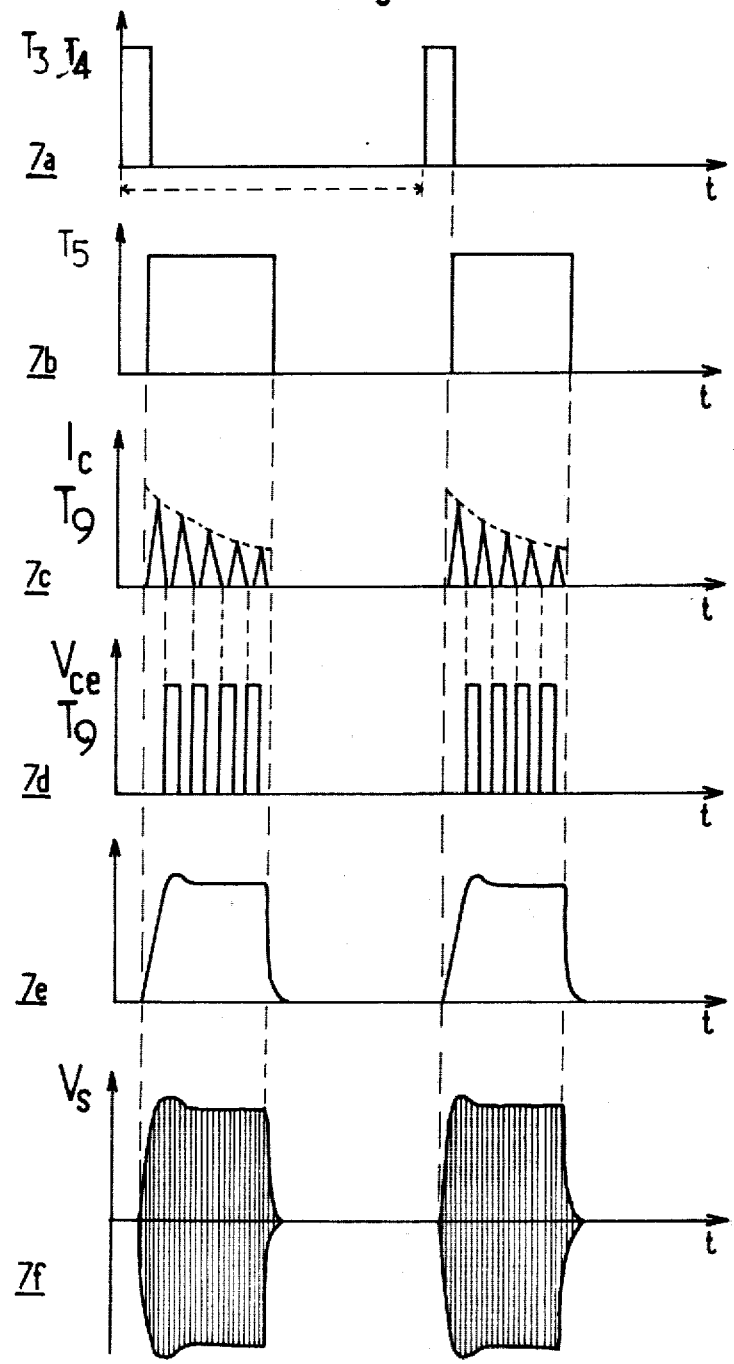

HIGH FREQUENCY VOLTAGE GENERATOR

BACKGROUND OF THE INVENTION

The present invention relates to a high frequency voltage generator which may be used more particularly, but not exclusively, for supplying an electric bistoury or lancet.

Presently known high frequency voltage generators of this type generally comprise a power oscillator which operates an output transformer whose secondary winding is connected between the cutting electrode of the bistoury and the neutral plate. This oscillator is most often supplied by a rectifier bridge followed by a switch whose role is to switch a capacitor either into "cutting" position in which the capacitor filters the waves from the mains, or into "coagulation" position in which the capacitor is disconnected, thus giving an output voltage modulated in amplitude by the mains of 10.0 Hz.

Known generators of this type present a certain number of drawbacks. In fact, as the impedance of a tissue is a decreasing function of the depth of cut and the output impedance of the lancets produced up to the present time is not negligible compared with the impedance of the tissues to be cut, a considerable drop in power is produced with these lancets, as soon as the electrode penetrates into the tissues, this being translated by a "sticking" of the electrode.

Inversely, if the operator displays, by means of a regulating element (potentiometer) a sufficient power to allow a deep cut, sparking is inevitably produced at the beginning and end of cut. From the clinical point of view, this is translated by necroses in the zones reached by electric arcs.

Furthermore, in the known high frequency voltage generators for supplying electric bistouries, the modulation of amplitude of the high frequency signal is not modifiable continuously, hence the impossibility of accurately determining the effect of coagulation during the different cuts.

SUMMARY OF THE INVENTION

It is an object of the present invention to remedy these drawbacks by providing a generator having a high operational reliability and of which the output power is always adapted in optimal manner to the cutting effort required.

To this end, this high frequency voltage generator which may be used particularly in surgery for supplying an electric bistoury, comprising a power oscillator operating an output transformer, is characterised in that it comprises a chopping supply placed in the direct control chain of the power oscillator.

According to a complementary feature of the invention, the output voltage of the generator is controlled by a first regulation loop whose reference value is increased by means of a positive feedback proportional to the output current. This system of double servo-control of the voltage and of the output current may not only enable the output impedance of the high frequency generator to be annulled, but may even render it strongly negative due to the energetic action of the positive feedback. One of the noteworthy features of the generator according to the invention is that a variable impedance intended generally for determining the power is not introduced in series with the output circuit. The generator according to the invention enables the power supplied to be adapted in all cases by the electric bistoury to the required effort of cut.

Moreover, means are provided to progressively and continuously adjust the dosage of the coagulation from pure high frequency to a chopping into very fine pulses.

BRIEF DESCRIPTION OF THE DRAWINGS

The invention will be more readily understood on reading the following description with reference to the accompanying drawings, in which:

FIGS. 6 and 7 are diagrams of the wave forms of signals appearing at various points of the circuit of the generator of FIG. 5, in "cutting" and "coagulation" position respectively of said generator.

DESCRIPTION OF THE PREFERRED EMBODIMENT

Figure 1:
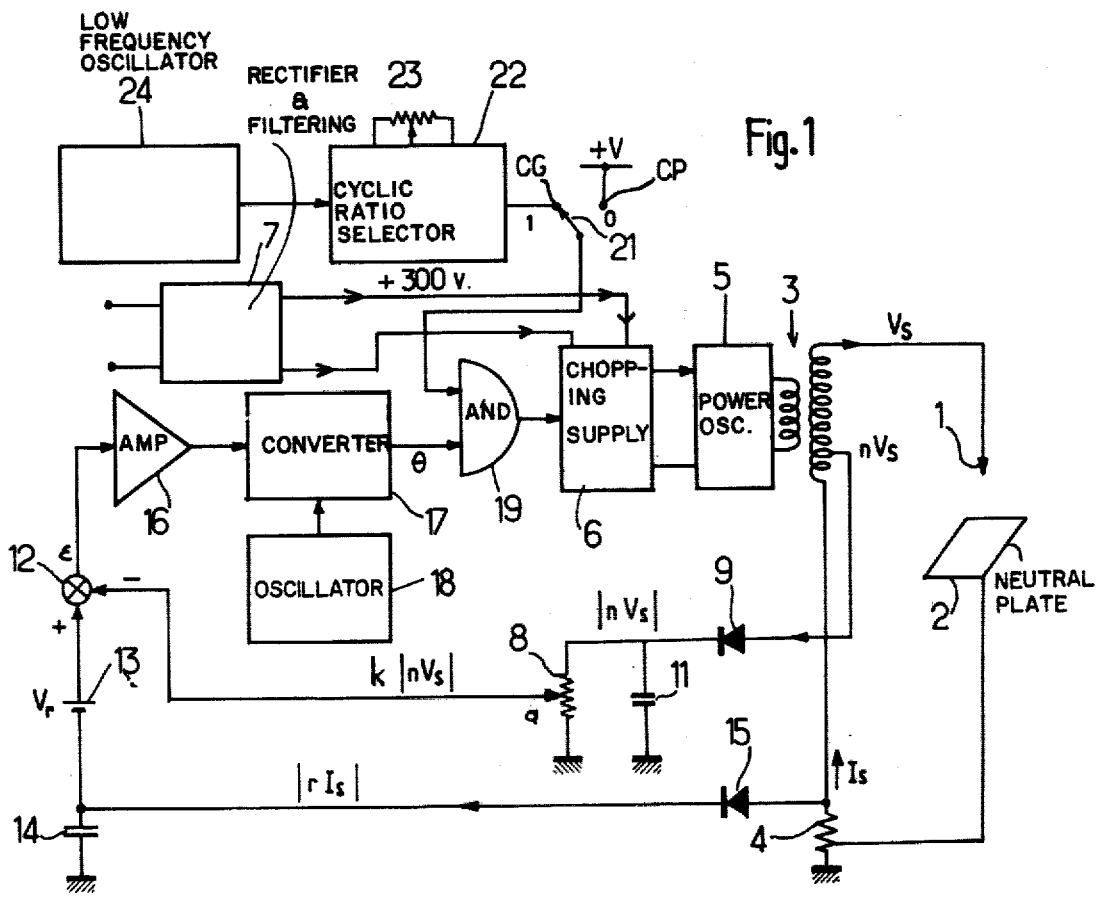
FIG. 1 is a block diagram of a high frequency voltage generator according to the invention.

Referring now to the drawings, FIG. 1 shows the essential elements constituting the high frequency voltage generator according to the invention. This generator is more particularly adapted to the supply of an electric bistoury comprising a cutting electrode 1 intended for cutting the tissues placed on a neutral plate 2 connected to earth. The electrode 1 is connected to one end of a secondary winding of an output transformer 3, supplying the high frequency voltage $V_s$ and the other end of which is connected to earth via a resistor 4. The transformer 3 is connected to the output of a power oscillator 5 operating for example at a frequency of 2 MHz.

According to the invention, the high frequency voltage generator comprises a chopping supply 6 which is placed in the direct control chain of the power oscillator 5. This supply 6 receives, from a rectifying and filtering stage 7, a D.C. voltage, for example of +300 V, the stage 7 being to this end connected to the mains.

The high frequency power supplied by the oscillator 5 is controlled by means of a double servo-control.

A first servo-control regulates the output voltage Vs to a value which is determined by a power potentiometer 8. This potentiometer is connected on the one hand to earth and on the other hand, via a diode 9, to an intermediate point of the secondary winding of the transformer 3 at which appears a fraction $nV_s$ of the output voltage. A capacitor 11 is moreover connected in parallel with the potentiometer 8.

The servo-control loop further comprises an error detector 12 which compares the fraction $nV_s$ of the amplitude of the output voltage with a reference voltage $V_r$ which is supplied in part by a constant source 13 and which may be modified by the second servo-control.

This second servo-control is a positive feedback proportional to the current absorbed by the tissue to be cut. To this end, the constant voltage source 13 is connected on the one hand to earth via a capacitor 14 and on the other hand, via a diode 15, to the point of junction between the resistor 4 and the end of the secondary winding of the output transformer 3. If r is the value of the resistor 4 and $I_s$ the intensity of the output current, the voltage $rI_s$, which represents information relative to the output current $I_s$, is added to the reference voltage $V_r$ of the servo-control loop in voltage, in other words the total reference voltage applied to an input of the error detector 12 is equal to the reference voltage $V_r$ supplied by the source 13 increased by the additional voltage $rI_s$.

The second input of the error detector 12 is connected to the cursor of the potentiometer 8 and this second input is therefore subjected to a voltage $knV_s$ which is a fraction of the output voltage $V_s$.

The error signal supplied by the detector 12 and which correspnds to the difference between the voltages $V_r + rI_s$ and $knV_s$ is applied to the input of an amplifier 16 whose output is connected to a converter 17 of the error voltage in cyclic ratio. This converter 17 is itself supplied by an oscillator 18 operating for example at a frequency of 20 kHz. The signal applied to the input of the converter 17 is used to vary the conduction time of the switch (transistor or thyristor) of this converter as a function of the level of the input voltage, and consequently to modify the cyclic ratio of the output signal as a function of the input signal.

The output signal of the converter 17 is applied to an input of an AND gate 19 whose output is connected to the chopping supply 6 and which comprises a second input connected from a switch 21 which may occupy two positions, namely, a "cutting" position CP and a "coagulation" position CG. In the "cutting" position CP, the switch 21 is connected to a source of positive voltage $+V$ whilst in the "coagulation" position CG, this switch is connected to the output of a cyclic ratio selector 22, provided with an adjusting potentiometer 23 and connected to a low frequency oscillator 24.

When the switch 21 is placed in "cutting" position CP, the AND gate 19 is permanently open and the output signal of the converter 17 is transmitted through the AND gate 19 to the cutoff supply 6. This supply allows a 90% yield whatever the power consumed. The converter 17 intervenes, as has been seen previously, to vary the conduction time of the switch of the converter 17 and consequently the power supplied to the oscillator 6, as a function of the amplitude of the error signal supplied by the detector 12. This results in a variation in the supply voltage of the oscillator 5 which causes a reduction and then a cancellation of the difference between the reference voltage and the fraction $knV_s$ of the output voltage $V_s$.

Figure 2:
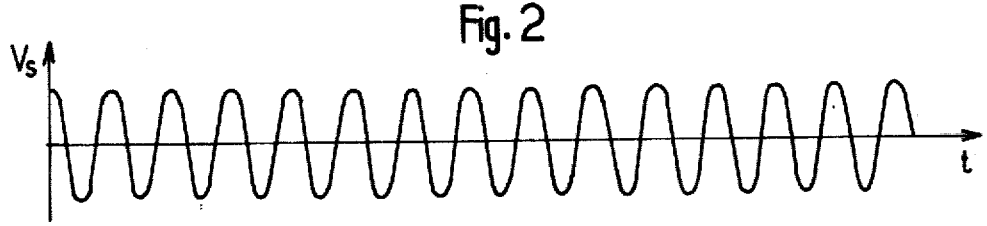
FIG. 2 is a diagram illustrating the shape of the high frequency output voltage in "cutting" position of the generator.

In this way, an A.C., high frequency output voltage $V_s$ is obtained as illustrated by the diagram of FIG. 2. The current information $rI_s$ which is added to the reference voltage $V_r$ of the servo-control loop in voltage has for its effect to increase the output voltage $V_s$ by a quantity proportional to the increase in the load.

In order to understand the combined effects of the two servocontrol loops more readily, it will firstly be assumed that the feedback in current is eliminated:

(a) Effect of the voltage regulation alone: The power supplied by the oscillator is in the form $$P = \frac{(Vs\ eff)}{2} Gu$$

Vs eff = effective output voltage
with
Gu = conductance of the load
Since the output voltage is controlled, $$Vs\ eff = K \quad P = \frac{K}{2} Gu$$

Figure 4:
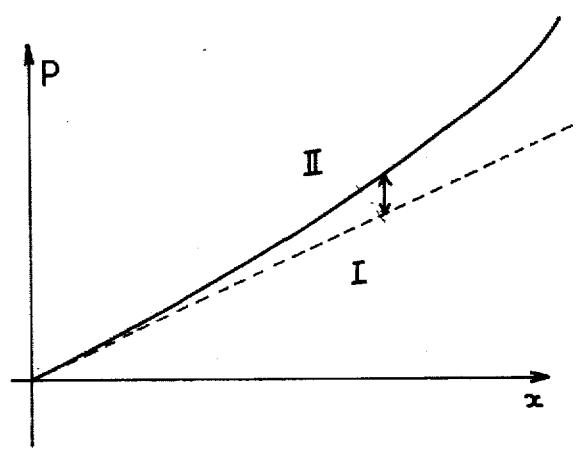
FIG. 4 is a diagram illustrating the variation in the power supplied by the generator according to the invention, as a function of the load.

The supplied power P is therefore proportional to the load, thus to the depth of cut, as is indicated by the broken-line curve $^I$ in the diagram of FIG. 4.

(b) Influence of the feedback in current combined with the servo-control of the output voltage.

The positive feedback in current increases the reference voltage of the servo loop in voltage, thus further accentuating the increase in the power P as a function of the load x, as is shown by the solid-line curve II of the diagram of FIG. 4.

Figure 3:
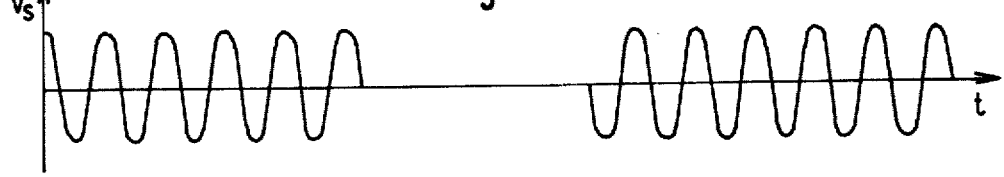
FIG. 3 is a diagram illustrating the variation in the high frequency output voltage in "coagulation" position of the generator.

When it is desired to effect a coagulation, the switch 21 is passed into CG position and, in this case, the second input of the AND gate 19 receives the output signal of the cyclic ratio selector 22. This signal is in fact that of the low frequency oscillator 24, whose cyclic ratio is modified by stage 22. Consequently, the pulses controlling the chopping supply 6 are periodically blocked by the AND gate 19 at the frequency of the oscillator 24 and for a period of time depending on the adjustment of the selector 22, thus causing interruptions of the output $V_s$ as shown in FIG. 3. The dosage of the coagulation is obtained by means of the potentiometer 23 whose role is to vary the cyclic ratio between 0 and 100%, this enabling a continuous variation to be obtained from pure high frequency (FIG. 2) to very fine pulses.

Figure 5:
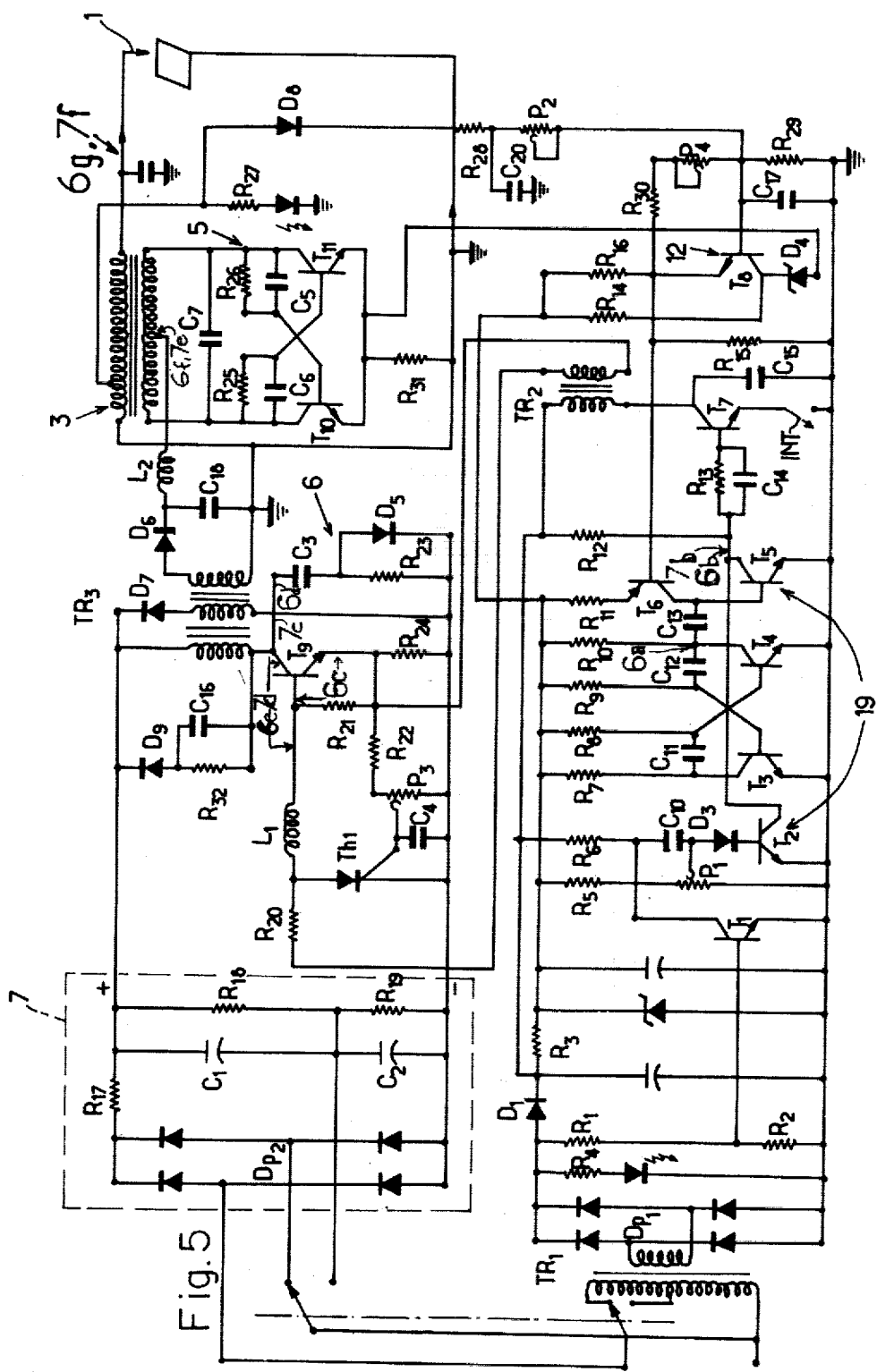
FIG. 5 is an electric diagram of an embodiment of the generator according to the invention.

A non-limiting embodiment of a high frequency voltage generator using the double servo control described previously will now be described with particular reference to FIG. 5.

The chopping supply 6 is effected by means of a switch transistor T9 chopping the D.C. high voltage ($+300$ V for example) obtained at the output of the rectifying and filtering stage 7 connected to the 220 V or 110 V mains, without passing via a 50 Hz transformer. This solution offers a considerable saving in weight, bulk and increased yield. The rectifying and filtering stage 7 comprises a rectifier bridge with diodes Dp2, a series resistor R17, two series capacitors $C_1$ and $C_2$ and two series resistors R18,R19.

The switch transistor T9 is blocked and controlled-in blocked and saturated state—at the frequency of 20 kHz by means of an optimised base circuit comprising a transformer TR2, a coil L1 and resistors R20 and R21. One of the ends of the secondary winding of the transformer TR2 is connected to an end of the resistor R20 which is connected, in series with the coil L1, to the base of the transistor T9. The resistor R21 is connected in parallel between the base and the emitter of this transistor and its end is connected to the other end of the secondary winding of the transformer TR2. A circuit for protecting the transistor T9 against short circuits is produced by means of a thyristor Th1 whose anode is connected to the point of junction between the resistor R20 and the coil L1, the cathode to the negative terminal of the rectifying stage 7 and the gate to the cursor of a potentiometer P3 and to an armature of a capacitor C4 also connected to the negative terminal. This protection circuit further comprises a resistor 22 connected between the potentiometer P3 and the emitter of the transistor T9 and a resistor R24 connected between this emitter and the negative terminal.

A protection network of the transistor T9 at opening is also provided. This network comprises a capacitor C3 connected to the collector of the transistor T9 and to the negative terminal of the rectifying stage 7, by means of a diode D5 and a resistor R23 in parallel.

The chopping supply 6, further, comprises a transformer TR3 having three windings, namely a primary winding branched between the collector of the transistor T9 and the positive terminal of the rectifying stage 7, a secondary winding connected to a rectifying and filtering cell comprising in series a diode D6 and a coil L2, and a capacitor C18 in parallel, and a third winding connected in series with a diode D7 between the positive and negative terminals. This third winding recovers the non-consumed or secondary energy (in the case of the high frequency oscillator 5 operating at low power), this enabling a 90% yield to be conserved, whatever the power necessary for cutting.

In parallel on the primary winding of the transformer TR3 is connected a network eliminating overvoltage, this network comprising a resistor R32 and a capacitor C16 in parallel, themselves connected in series with a diode D9.

The diagram of the high frequency oscillator 5 is conventional: it is constituted by an a stable mulivibrator with two transistors T10, T11, associated with capacitors. C5,C6 and with resistors R25,R26, this multivibrator supplying in push-pull the primary winding of the output transformer 3. A capacitor C7 is connected in parallel to this winding.

This secondary winding of the output transformer 3 comprises an intermediate point which is connected to earth via a resistor R27 and which furnishes information proportional to the amplitude of the output voltage. The current information is taken at the terminals of a resistor R31 connected between the emitters of the two transistors T10, T11 and earth.

The two pieces of information necessary for double servo-control namely the voltage information and current information, are applied to the error detector comparator 12 constituted by a transistor T8 and a resistor 16. To this end, the intermediate point of the secondary winding of the output transformer 3 is connected to the base of the transistor T8 via a diode D8, a resistor R28 and a potentiometer P2 connected in series, the point of junction between the resistor R28 and the potentiometer P2 being connected to earth via a capacitor C20. The base of the transistor T8 is connected to earth by a resistor R29 and a capacitor C17 in parallel and it is connected to its collector by a potentiometer P4 and a resistor R30. The emitter of the transistor T8 is connected, via a resistor R14, to a D.C. supply comprising a transformer TR1 connected to the mains, a rectifier bridge with diodes Dp1, and a series diode D1. This emitter is also connected to the two transistors T10, T11, i.e. to the resistor R31, via a Zener diode D4 furnishing the reference voltage of the servo-control.

The collector of the transistor T8 is connected to one end of the resistor R16, the other end of which is connected to the diode D1, via a resistor R3, to the base of a transistor T6, and to earth by a resistor R15.

It is seen from the above that the reference voltage of the servo-control is furnished by the Zener diode D4 connected in series with the current information given by the resistor R31, the display of the output power is effected by the potentiometric divider constituted by the potentiometer P2 and the resistor R29, and the stop resistor R28 is to fix the minimum of the output voltage.

The amplified error signal which appears on the collector of the transistor T8, is applied to the base of the transistor T6 mounted as a current generator. This transistor T6 is closely associated with transistors T3,T4 and T5 to effect the error voltage/cyclic ratio conversion necessary for controlling the chopping supply.

The transistors T3 and T4 are mounted as an astable multivibrator operating at the frequency of 20 kHz. To this end, their emitters are connected to earth and their collectors and bases are interconnected conventionally by capacitors C11,C12 and transistors R7, R8, R9, R10. A capacitor C13 connects the collector of the transistor T4 to that of the transistor T6 whose emitter is connected to the positive terminal of the supply by a resistor R11. The collector of the transistor T6 is connected, furthermore, to the base of the transistor T5, the emitter of which is connected to earth and the collector is connected to the positive terminal by a resistor R12. This transistor T5 operates as a monostable multivibrator of which the duration of the metastable state is variable due to the current generator constituted by the transistor T6 and the resistor R11.

The circuit further comprises a transistor T1 whose emitter is connected to earth, the collector to the positive supply terminal via a resistor R6, and the base to the point of junction of a supply voltage divider constituted by two resistors R1 and R2 in series. This transistor T1 which is associated with the bridge $DP_1$ and with the diode D1 produces pulses of frequency 100 Hz synchronous with the mains. These pulses are applied, through a capacitor C10 and a diode D3, to the base of a transistor T2 constituting a monostable multivibrator. The point of junction between the capacitor C10 and the diode D3 is connected to the the cursor of a potentiometer P1 connected in series with a resistor R5 to the supply terminals. The transistor T2 then operates in blocked-saturated state at the frequency of 20 kHz with a cyclic ratio proportional to the amplified error voltage. The duration of the metastable stage of the transistor T2 is variable between 0 and 10% by means of the potentiometer P1.

The collector of the transistor T2 is connected, via a resistor R13 and a capacitor C14 in parallel, to the base of a transistor T7, the emitter of which may be connected to earth by a stop-start switch INT, and the collector of which is connected on the one hand to earth via a capacitor C15 and on the other hand to one end of the primary winding of the insulation transformer TR2, the other end of which is connected to the positive terminal of the supply.

The interruptions necessary for coagulation are produced by the assembly comprising the rectifier bridge Dp1, the diode D1 and the transistors T1 and T2. The transistor T2 is associated with transistor T5 to form the logic AND gate 19 for blocking the pulses at 20 kHz at the rhythm of the signal at 100 Hz. The signals corresponding to the "chopping" mode are represented in FIGS. 3 and 7. The signals represented by the diagrams 7a, 7b, 7c, 7d, 7e, and 7f appear at the various points of the circuit shown in FIG. 5, which are given these same references.

The complete stopping of the "chopping" at 100 Hz may be ensured by connecting the cursor of the potentiometer P1 to earth. In this case, the transistor T2 is blocked, this allowing free passage of the pulses controlling the chopping supply, therefore the functioning in pure high frequency. This functioning is illustrated by the diagrams of FIG. 6 and there again the elementary diagrams 6a, 6b, 6c, 6d, 6e, 6f, and 6g correspond to signals appearing at the points marked correspondingly in the diagram of FIG. 5.

One of the remarkable features of the generator according to the invention is that it does not introduce in series with the output circuit a variable impedance intended generally for dosing the power.

It should be noted that in the generator according to the invention, the system of double servo-control does not content itself with annulling the output impedance of the HF generator; it even renders its strongly negative due to the energetic action of the positive feedback.

What I claim is:

1. A high frequency voltage generator, usable in particular in surgery for supplying an electric bistoury or lancet, comprising a rectifying and filtering stage connected to electric mains supply, a high frequency power oscillator, an output transformer supplied by said high frequency power oscillator, a chopping supply connected to said high frequency oscillator and connected to the output of said rectifying and filtering stage, the chopping frequency of said chopping supply being much higher than that of said mains supply, an error detector having two inputs, means for applying to a first input of said error detector a first signal corresponding to information relative to the voltage taken from the output transformer of the high frequency oscillator, means for applying to the second input of said error detector a second signal corresponding to information relative to the current of the high frequency power oscillator, said error detector being connected to the chopping supply to control said chopping supply;

first and second regulation loops respectively connected to said first and said second inputs of said error detector, said first regulation loop providing for the servo-control of the output voltage from said output transformer while said second loop provides a positive feedback proportional to current in a tissue to be cut which increases the reference voltage of the output voltage proportionally to the output current, said two servo-control loop rendering the output impedance of the generator negative;

said first regulation loop extending between an intermediate point of the secondary winding of said output transformer and said first input of said error detector and comprising a first potentiometer for adjusting the output power, said second regulation loop comprising a circuit through which passes a current proportional to the output current and connected to a pole of a source of voltage, the other pole of which is connected to the second input of said error detector and which supplies a reference voltage; and a first transistor constituting a monostable multivibrator, a second transistor triggering said first transistor at each beginning of alternation, a third transistor from the collector of which are taken pulses controlling said chopping supply and which are interrupted by said second transistor, and a second potentiometer connected so as to continuously to vary the time during which said chopping supply control pulses are interrupted, from long interruptions in the case of strong coagulation to the total absence of interruption in the case of a pure cut.

2. The generator of claim 1, comprising an amplifier and a voltage/cyclic ratio converter between said error detector and said chopping supply, the output of said voltage/cyclic ratio converter being connected to the input of said chopping supply, and a second oscillator supplying said voltage/cyclic ratio converter.

3. The generator of claim 1 or 2, comprising a stage varying the cyclic ratio and said second potentiometer being connected to said last-mentioned stage in order progressively and continuously to adjust the dosage of coagulation from pure high frequency to a chopping into very fine pulses.

4. A high frequency voltage generator for use in surgery to supply power to an electric bistoury or lancet responsive to the depth of tissue to be cut and cutting effort required, comprising:

a rectifying and filtering stage connected to electric mains supply, a high frequency power oscillator, an output transformer supplied by said high frequency power oscillator, a chopping supply connected to said high frequency power oscillator in the direct control chain thereof and connected to the output of said rectifying and filtering stage, the chopping frequency of said chopping supply being much higher than that of said supply means, an error mains, an error detector having two inputs and a single output, means for applying to the first input of said error detector a first signal corresponding to information relative to the voltage directly taken from the output transformer of said high frequency oscillator, means for applying to the second input of said error detector a second signal corresponding to information relative to the current of said high frequency power oscillator, said error detector being responsive to said first and said second inputs to produce said signal output and being connected to said chopping supply for control thereof by said single output;

first and second regulation loops respectively connected to said first and said second inputs of said error detector, said first regulation loop providing for the servo-control of the output voltage while said second loop constitutes a positive feed back proportional to current related to the depth of the tissue to be cut which increases the reference voltage of the output voltage proportionally to the output current, said two servo-control loops rendering the output impedance of the generator neagtive; and, said first regulation loop extending between an intermediate point of the secondary winding of the output transformer and the first input of said error detector and comprising a first potentiometer for adjusting the output power, and said second regulation loop comprising a circuit through which passes a current proportional to the output current and connected to a pole of a source of voltage, the other pole of which is connected to the second input of said error detector and which supplies a reference voltage.

5. The generator of claim 4, comprising a first transistor constituting a monostable multivibrator, a second transistor triggering said first transistor at each beginning of alternation, a third transistor from the collector of which are taken pulses controlling said chopping supply and which are interrupted by said second transistor, and a second potentiometer connected so as continuously to vary the time during which said chopping supply control pulses are interrupted, from long interruptions in the case of strong coagulation to the total absence of interruption in the case of a pure cut.

6. The generator of claim 5 comprising a stage varying the cyclic ratio and said second potentiometer connected to said stage in order progressively and continuously to adjust the dosage of coagulation from pure high frequency to a chopping into very fine pulses.

7. The generator of claim 4, comprising an amplifier and a voltage/cyclic ratio converter between said error detector and said chopping supply, the output of said voltage/cyclic ratio converter being connected to the input of said chopping supply, and a second oscillator supplying said voltage/cyclic ratio converter.

* * * * *